US009751823B2

(12) United States Patent
Sun et al.

(10) Patent No.: US 9,751,823 B2
(45) Date of Patent: Sep. 5, 2017

(54) PROCESSES FOR MAKING METHACRYLIC ACID

(71) Applicants: Archer Daniels Midland Company, Decatur, IL (US); Washington State University, Pullman, WA (US)

(72) Inventors: Junming Sun, Pullman, WA (US); Changjun Liu, Pullman, WA (US); Yong Wang, Pullman, WA (US); Kevin Martin, Mt. Zion, IL (US); Padmesh Venkitasubramanian, Forsyth, IL (US)

(73) Assignees: Archer Daniels midland Co., Decatur, IL (US); Washington state University, Pullman, WA (US)

( * ) Notice: Subject to any disclaimer, the term of this patent is extended or adjusted under 35 U.S.C. 154(b) by 0 days.

(21) Appl. No.: 15/183,991

(22) Filed: Jun. 16, 2016

(65) Prior Publication Data
US 2016/0289155 A1   Oct. 6, 2016

Related U.S. Application Data

(60) Division of application No. 14/683,257, filed on Apr. 10, 2015, now Pat. No. 9,403,749, which is a continuation of application No. PCT/US2013/067036, filed on Oct. 28, 2013, said application No. 14/683,257 is a continuation of application No. PCT/US2013/063968, filed on Oct. 9, 2013, said application No. 14/683,257 is a (Continued)

(51) Int. Cl.
*C07C 51/25*   (2006.01)
*C07C 45/35*   (2006.01)
*C07C 1/20*   (2006.01)
*C07C 1/207*   (2006.01)
*B01J 23/06*   (2006.01)

(52) U.S. Cl.
CPC ............. *C07C 51/252* (2013.01); *B01J 23/06* (2013.01); *C07C 1/20* (2013.01); *C07C 1/2074* (2013.01); *C07C 1/2078* (2013.01); *C07C 45/35* (2013.01); *C07C 2521/06* (2013.01); *C07C 2523/06* (2013.01)

(58) Field of Classification Search
None
See application file for complete search history.

(56) References Cited

U.S. PATENT DOCUMENTS 3,692,693 A * 9/1972 Gunning .................. B01J 23/96
                                                            208/140
8,273,313 B2 * 9/2012 Galloway ............... C07C 51/42
                                                            422/129

(Continued)

OTHER PUBLICATIONS

Sun et al. (J. Am. Chem. Soc., 2011(133) 11096).*

*Primary Examiner* — Sudhakar Katakam
*Assistant Examiner* — Jennifer C Sawyer
(74) *Attorney, Agent, or Firm* — William B. Miller

(57) ABSTRACT

Processes are described for making methacrylic acid via methacrolein from a biobased isobutene, wherein the biobased isobutene is prepared from ethanol or from acetic acid in the presence of a $Zn_xZr_yO_z$ mixed oxide catalyst, the biobased isobutene is oxidized to methacrolein and the methacrolein is further oxidized to methacrylic acid.

4 Claims, 2 Drawing Sheets

Related U.S. Application Data continuation of application No. PCT/US2013/062784, filed on Oct. 1, 2013.

(60) Provisional application No. 61/844,998, filed on Jul. 11, 2013, provisional application No. 61/737,312, filed on Dec. 14, 2012, provisional application No. 61/720,433, filed on Oct. 31, 2012.

(56) References Cited

U.S. PATENT DOCUMENTS

| | | | |
|---|---|---|---|
| 2009/0113787 A1* | 5/2009 | Elliott | B01J 23/462 44/308 |
| 2009/0123364 A1* | 5/2009 | Forsyth | C01B 3/34 423/651 |

* cited by examiner

PROCESSES FOR MAKING METHACRYLIC ACID

CROSS-REFERENCE TO RELATED APPLICATIONS

The present application is a divisional application from U.S. patent application Ser. No. 14/683,257, filed Apr. 10, 2015, which was a continuation of International Application No. PCT/US2013/067036 filed Oct. 28, 2013, now published as WO 2015/005942, which directly claims the benefit of U.S. Provisional Application Ser. No. 61/844,998, filed Jul. 11, 2013; the U.S. patent application Ser. No. 14/683,257 was also a continuation of International Application No. PCT/US2013/063968 filed Oct. 9, 2013, now published as WO 2014/092849, which directly claims the benefit of U.S. Provisional Application Ser. No. 61/737,312 filed Dec. 14, 2012; and, the U.S. patent application Ser. No. 14/683,257 was also a continuation of International Application No. PCT/US2013/062784 filed Oct. 1, 2013, now published as WO 2014/070354, which directly claims the benefit of U.S. Provisional Application Ser. No. 61/720,433 filed Oct. 31, 2012.

TECHNICAL FIELD OF THE INVENTION

The present application concerns processes for making methacrylic acid via methacrolein from isobutene.

BACKGROUND ART

In this regard, isobutene is widely used for the production of a variety of industrially important products, and has been used to make methacrylic acid via methacrolein in one commercially known route. Isobutene has however been produced commercially to date through the catalytic or steam cracking of fossil feedstocks. As fossil resources are depleted and/or become more costly to use, renewable source-based routes to isobutene are increasingly needed—especially in consideration of increased demand for isobutene.

A hard-template method has previously been described for synthesizing $Zn_xZr_yO_z$ mixed oxides for the direct and high yield conversion of ethanol (from the fermentation of carbohydrates from renewable source materials, including biomass) to isobutene, wherein ZnO was added to $ZrO_2$ to selectively passivate zirconia's strong Lewis acidic sites and weaken Brönsted acidic sites while simultaneously introducing basicity. The objectives of the hard template method were to suppress ethanol dehydration and acetone polymerization, while enabling a surface basic site-catalyzed ethanol dehydrogenation to acetaldehyde, an acetaldehyde to acetone conversion via aldol-condensation/dehydrogenation, and a Brönsted and Lewis acidic/basic site-catalyzed acetone-to-isobutene reaction pathway.

High isobutene yields were in fact realized, but unfortunately, as later experienced by Mizuno et al. (Mizuno et al., "One-path and Selective Conversion of Ethanol to Propene on Scandium-modified Indium Oxide Catalysts", Chem. Lett., vol. 41, pp. 892-894 (2012)) in their efforts to produce propylene from ethanol, it was found that further improvements in the catalyst's stability were needed.

SUMMARY OF THE INVENTION

Our U.S. Patent Application Ser. No. 61/720,433 (the "'433 application"), filed Oct. 31, 2012 for "Stable Mixed Oxide Catalysts for Direct Conversion of Ethanol to Isobutene and Process for Making", concerned the discovery that these improvements could be realized without adding modifying metals and without a reduction in the initial high activity (100 percent ethanol conversion) that had been observed in these mixed oxide catalysts. The '433 application thus in sum concerned an improved stability, longer lifetime catalyst for converting ethanol to isobutene.

Separately, we discovered that acetic acid, rather than ethanol, may be converted to a biobased isobutene product using certain mixed oxide catalysts, including a mixed oxide catalyst as made in the '433 application. This discovery became the basis for U.S. Patent Application Ser. No. 61/737,312 (the "'312 application"), filed Dec. 14, 2012 for "Process and Catalyst for Conversion of Acetic Acid to Isobutene".

Building on these discoveries, the present invention in one aspect concerns a process for making methacrylic acid via methacrolein from a biobased isobutene, wherein the biobased isobutene is prepared from ethanol in the presence of a $Zn_xZr_yO_z$ mixed oxide catalyst, the biobased isobutene is oxidized to methacrolein and the methacrolein is oxidized to methacrylic acid.

In certain embodiments according to this first aspect, the $Zn_xZr_yO_z$ mixed oxide catalyst exhibits improved stability for the conversion, exhibiting less than 10 percent loss, more preferably less than 5 percent loss and still more preferably less than 2 percent loss in isobutene selectivity over a period of 200 hours on stream. In other embodiments, the $Zn_xZr_yO_z$ mixed oxide catalyst is made by a process as described in the '433 application, broadly comprising forming a solution of one or more Zn compounds, combining one or more zirconium-containing solids with the solution of one or more Zn compounds, drying the wetted solids, then calcining the dried solids.

In a second, related aspect, the present invention concerns a process for making methacrylic acid via methacrolein from a biobased isobutene, wherein the biobased isobutene is prepared from acetic acid in the presence of a catalyst, the biobased isobutene is oxidized to methacrolein and the methacrolein is oxidized to methacrylic acid. In certain embodiments, the catalyst is a $Zn_xZr_yO_z$ mixed oxide catalyst, especially a catalyst made by a process as described in the '433 application, and the process of making the starting biobased isobutene is carried out as described in the '312 application.

DESCRIPTION OF EMBODIMENTS

Figure 1:
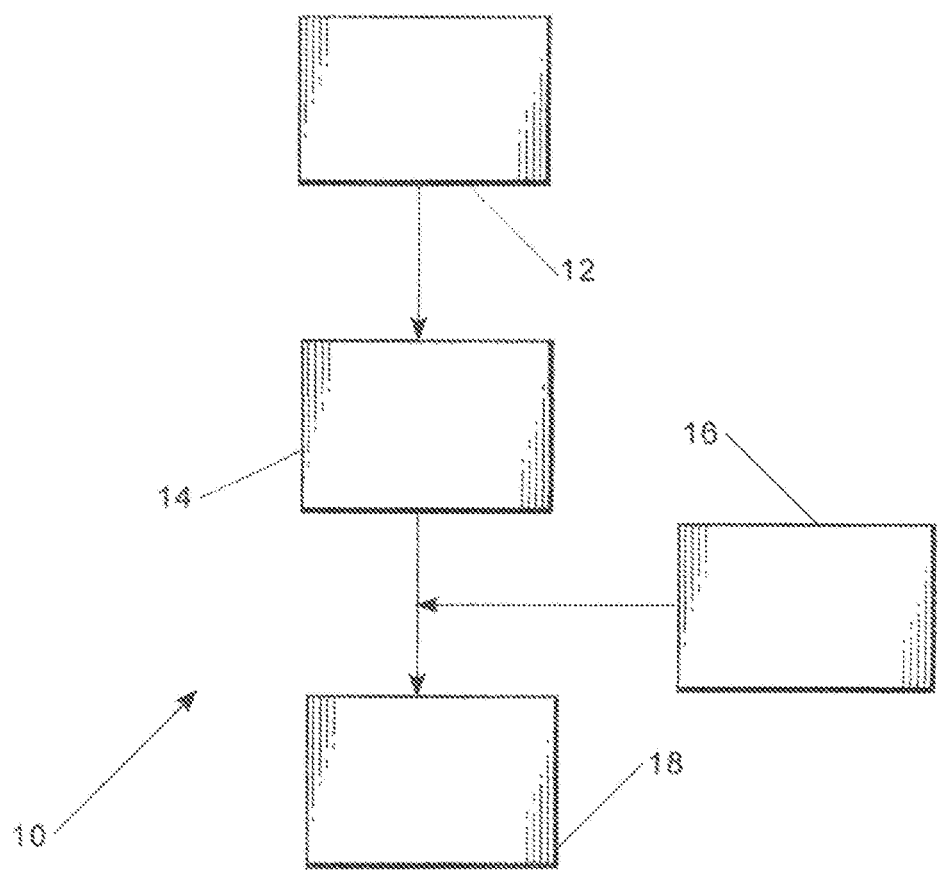
FIG. 1 schematically depicts a process for producing a wholly biobased methacrylic acid from a wholly biobased isobutene made from ethanol in the presence of a $Zn_xZr_yO_z$ mixed oxide catalyst, especially such a catalyst made by a process as described in the '433 application.

Referring now to FIG. 1, a process 10 is schematically illustrated wherein ethanol 12 is converted to isobutene 14 in the presence of a catalyst, particularly, a $Zn_xZr_yO_z$ mixed oxide catalyst. The isobutene 14 is then combined with oxygen from an oxygen source 16 and oxidized to yield methacrolein, which is then oxidized with oxygen from oxygen source 16 to provide a methacrylic acid product 18.

The ethanol 12 is conventionally derived from biological carbon sources, for example, by fermentation of five- and especially six-carbon sugars, so that the isobutene 14 and subsequent methacrylic acid product 18 are desirably wholly-biobased.

Parenthetically, by "biobased", we mean those materials whose carbon content is shown by ASTM D6866 to be derived from or based in significant part (at least 20 percent or more) upon biological products or renewable agricultural materials (including but not being limited to plant, animal and marine materials) or forestry materials. "Wholly biobased" thus will be understood as referring to materials whose carbon content by ASTM D6866 is entirely or substantially entirely (for example, 95 percent or more) indicated as of biological origin.

In this respect ASTM Method D6866, similar to radiocarbon dating, compares how much of a decaying carbon isotope remains in a sample to how much would be in the same sample if it were made of entirely recently grown materials. The percentage is called the biobased content of the product. Samples are combusted in a quartz sample tube and the gaseous combustion products are transferred to a borosilicate break seal tube. In one method, liquid scintillation is used to count the relative amounts of carbon isotopes in the carbon dioxide in the gaseous combustion products. In a second method, 13C/12C and 14C/12C isotope ratios are counted (14C) and measured (13C/12C) using accelerator mass spectrometry. Zero percent 14C indicates the entire lack of 14C atoms in a material, thus indicating a fossil (for example, petroleum based) carbon source. One hundred percent 14C, after correction for the post-1950 bomb injection of 14C into the atmosphere, indicates a modern carbon source. ASTM D6866 effectively distinguishes between biobased materials and petroleum derived materials in part because isotopic fractionation due to physiological processes, such as, for example, carbon dioxide transport within plants during photosynthesis, leads to specific isotopic ratios in natural or biobased compounds. By contrast, the 13C/12C carbon isotopic ratio of petroleum and petroleum derived products is different from the isotopic ratios in natural or bioderived compounds due to different chemical processes and isotopic fractionation during the generation of petroleum. In addition, radioactive decay of the unstable 14C carbon radioisotope leads to different isotope ratios in biobased products compared to petroleum products.

The ethanol 12 can in this regard be derived from any known process whereby five and/or six carbon sugars from conventional grain milling operations or from processing of a lignocellulosic biomass more generally may be converted to one or more products inclusive of ethanol, at least in some part by fermentation means. Both aerobic and anaerobic processes are thus contemplated, using any of the variety of yeasts (e.g., *kluyveromyces lactis, kluyveromyces lipolytica, saccharomyces cerevisiae, s. uvarum, s. monacensis, s. pastorianus, s. bayanus, s. ellipsoidues, candida shehata, c. melibiosica, c. intermedia*) or any of the variety of bacteria (e.g., *clostridium sporogenes, c. indolis, c. sphenoides, c. sordelli, candida bracarensis, candida dubliniensis, zymomonas mobilis, z. pomaceas*) that have ethanol-producing capability from five and/or six carbon sugars under aerobic or anaerobic conditions and other appropriate conditions. The particular yeasts (or bacteria) used and other particulars of the fermentations employing these various yeasts (or bacteria) are a matter for routine selection by those skilled in the fermentation art.

However obtained, the ethanol 12 is then according to a first aspect of the invention converted to isobutene 14 in the presence preferably of a $Zn_xZr_yO_z$ mixed oxide catalyst as described in the '433 application, having excellent stability for the conversion of ethanol to isobutene in exhibiting less than 10 percent loss in isobutene selectivity over a period of 200 hours on stream under atmospheric pressure (<5 psig) and at 450° C., at full conversion of the ethanol 12 to the isobutene 14. Preferably, however, the catalyst exhibits less than 5 percent loss in isobutene selectivity over a period of 200 hours on stream, and more preferably less than 2 percent.

These $Zn_xZr_yO_z$ mixed oxide catalysts are generally characterized by a Zn/Zr ratio (x:y) of from 1:100 to 10:1, preferably from 1:30 to 1:1, especially 1:20 to 1:5, and still more preferably 1:12 to 1:10.

Parenthetically, in the present application where any range of values is given for any aspect or feature of the mixed oxide catalysts or any process described for using the mixed oxide catalysts, the given ranges will be understood as disclosing and describing all subranges of values included within the broader range. Thus, for example, the range of 1:100 to 10:1 will be understood as disclosing and describing not only the specific preferred and more preferred subranges given above, but also every other subrange including a value for x between 1 and 10 and every other subrange including a value for y between 1 and 100.

The catalysts made by the method of the '433 application are consistent in their particle size with catalysts made by the hard template method described in Sun et al., "Direct Conversion of Bio-ethanol to Isobutene on Nanosized $Zn_xZr_yO_z$ Mixed Oxides with Balanced Acid-Base Sites", Journal of the American Chemical Society, vol. 133, pp 11096-11099 (2011), wherein carbon black (BP 2000 carbon black from Cabot Corp.) was used as a hard template for the synthesis of nanosized $Zn_xZr_yO_z$ mixed oxides. In the hard template method of manufacture described in Sun, the BP 2000 template was dried at 180° C. overnight. Calculated amounts of zirconyl nitrate hydrate (Sigma-Aldrich, greater than 99.8% purity) and $Zn(NO_3)_2 \cdot 6H_2O$ (Sigma-Aldrich, greater than 99.8% purity) were dissolved in a given amount of water, and sonicated for 15 minutes to produce a clear solution with desired concentrations of Zn and Zr. About 25 grams of the obtained solution were then mixed with 6.0 grams of the preheated BP 2000 to achieve incipient wetness, and the mixture was transferred to a ceramic crucible and calcined at 400 degrees Celsius for 4 hours, followed by ramping the temperature to 550 degrees Celsius (at a ramp rate of 3 degrees Celsius/minute) and holding at 550 degrees Celsius for another 20 hours. Nanosized white powders were obtained, having a mean particle size of less than 10 nanometers. The catalysts made by the method of the '433 application and used in the method of FIG. 1 (for converting ethanol 12 to isobutene 14) likewise comprise aggregates of less than 10 nm-sized particles, with a highly crystalline structure. The Zn oxide component is again highly dispersed on the Zr oxide component.

As summarized in the '433 application, some characteristic differences have, however, also been observed between catalysts of equivalent Zn/Zr ratios made by the prior hard template method and by the method of the '433 application. For example, average crystallite size as calculated based on the Scherer equation will typically be larger, for example, 8.4 nanometers for a $Zn_1Zr_{10}O_2$ mixed oxide catalyst prepared according to the '433 application as compared to 4.8 nanometers for a $Zn_1Zr_{10}O_2$ mixed oxide catalyst prepared according to the former hard template method.

A $Zn_1Zr_{10}O_2$ mixed oxide catalyst prepared according to the method of the '433 application also has a smaller surface area, roughly 49 square meters per gram, as compared to 138 square meters per gram for a $Zn_1Zr_{10}O_2$ mixed oxide catalyst prepared according to the former hard template method.

One further, compositional difference was also observed between catalysts prepared by the two methods, in that the $Zn_xZr_yO_z$ mixed oxide catalysts according to the '433 application preferably are substantially sulfur-free, containing less than 0.14 weight percent of sulfur, as compared to, for example, 3.68 weight percent of sulfur in the same $Zn_1Zr_{10}O_2$ mixed oxide catalyst prepared according to the former hard template method.

The $Zn_xZr_yO_z$ mixed oxide catalysts of the '433 application and preferred for use herein have improved stability for the conversion of ethanol 12 to isobutene 14; while the contributions if any of the larger crystallite size and smaller surface area to this improved stability are not presently understood, it is nevertheless believed that at least the much reduced sulfur content of the inventive catalysts does contribute materially to this improved stability.

Based on infrared analyses of catalysts prepared according to the '433 application and according to the hard template method (which analyses are described more fully in the incorporated '433 application), the presence of sulfur in the former catalysts—presumably left behind from the Cabot BP 2000 furnace black hard template after the template's being substantially removed by a controlled combustion—appeared to have contributed to the presence of a number of stronger Lewis and Brönsted acidic sites on catalysts made by the former method and in turn to a greater degree of acidic site-catalyzed coking of catalysts made according to the former hard template method.

Accordingly, while from one perspective the $Zn_xZr_yO_z$ mixed oxide catalysts preferred for use in the present invention can be characterized in practice as having improved stability for the conversion of ethanol to isobutene, exhibiting less than 10 percent loss in isobutene selectivity over a period of 200 hours on stream, from a different, compositional perspective the preferred more stable $Zn_xZr_yO_z$ mixed oxide catalysts can be characterized as containing less than 0.14 percent by weight of sulfur. Preferably, still more stable catalysts are provided, having a sulfur content of less than 0.01 percent by weight, and still more preferably the catalysts will have a sulfur content of less than 0.001 percent by weight.

Such catalysts may be made by a process broadly comprising, in certain embodiments, forming a solution of one or more Zn compounds, combining one or more zirconium-containing solids with the solution of one or more Zn compounds so that the solution wets the zirconium-containing solids to a state of incipient wetness, drying the wetted solids, then calcining the dried solids. In other embodiments, a solution is formed of one or more Zr compounds, the solution is combined with one or more Zn-containing solids so that the solution wets the Zn-containing solids to a state of incipient wetness, the wetted solids are dried and then the dried solids are calcined. In principle, provided the zinc and zirconium compounds and solids in these embodiments do not contain sulfur, any combination of zinc and zirconium materials and any solvent can be used that will permit the zinc and zirconium components to mix homogeneously whereby, through incipient wetness impregnation, one of the zinc or zirconium components are well dispersed on a solid of the other component for subsequent drying and conversion to the oxide forms through calcining.

The conditions and times for the drying and calcining steps will depend, of course, on the particular zinc and zirconium materials and solvent used, but in general terms, the drying step can be accomplished in a temperature range of from 60 degrees Celsius to 200 degrees Celsius over at least about 3 hours, while the calcining can take place at a temperature of from 300 degrees Celsius to 1500 degrees Celsius, but more preferably a temperature of from 400 to 600 degrees Celsius is used. The calcination time can be from 10 minutes to 48 hours, with from 2 to 10 hours being preferred.

In still other embodiments, suitable $Zn_xZr_yO_z$ mixed oxide catalysts can also be prepared by a hard template method, except that a suitable very low sulfur content carbon is used for the hard template such that the finished catalyst will contain not more than 2 percent by weight of sulfur, especially not more than 0.5 percent by weight of sulfur and still more preferably will contain not more than 0.1 weight percent (by total weight of the catalyst) of sulfur. A variety of such very low sulfur carbons are available commercially from various suppliers; in general, the lower the sulfur content, the better for forming the highly active, stable mixed oxide catalysts preferred for use in a process of the present invention (whether based on ethanol as in FIG. 1 or acetic acid as in FIG. 2).

Processes for converting the ethanol 12 to isobutene 14 using these catalysts may be conducted in a manner and under conditions described in the Sun journal article, or in a manner and under conditions described in Mizuno et al or the several other prior publications concerned with the production of products inclusive of isobutene from ethanol. In this regard, while Mizuno et al. is particularly directed to the production of propylene from ethanol, it is nevertheless considered to be well within the capabilities of those skilled in the art to determine what conditions embraced by Mizuno et al. or other similar references will be most appropriate to produce isobutene among the possible products, without undue experimentation. Accordingly, a detailed description of process details for using the more stable mixed oxide catalysts need not be undertaken herein. Nevertheless, as an example, a continuous fixed bed reactor or flow bed reactor can be used. The reaction temperature may be in a range from 350 to 700 degrees Celsius, preferably, in a range from 400 to 500 degrees Celsius, and the WHSV can be in a range from 0.01 $hr^{-1}$ to 10 $hr^{-1}$, preferably from 0.05 $hr^{-1}$ to 2 $hr^{-1}$. Ethanol/water solution with steam to carbon ratios from 0 to 20, preferably from 2 to 5 can be used.

Once the isobutene 14 is formed, the isobutene 14 is oxidized with oxygen from an oxygen source 16 to yield methacrolein according to any known process and using any known catalyst for this purpose, and the methacrolein is further oxidized to produce a methacrylic acid product 18, again according to any known process and using any known catalyst for the second oxidation step from methacrolein to methacrylic acid.

A number of patents have been issued describing methods for producing methacrylic acid from isobutene via a methacrolein intermediate, though those skilled in the art will be aware that the following are given as merely non-limiting examples of the various processes and catalysts that have been and continue to be described in the patent and general scientific literature relating to a part of such a process or the process as a whole.

U.S. Pat. No. 8,273,313 to Galloway describes a system and process for separating methacrolein from methacrylic acid and acetic acid in the gas phase product from a partial oxidation of isobutene in two oxidation steps, purportedly maximizing recovery of all three components at minimum capital and energy cost, under conditions minimizing polymerization and plugging by solids deposition in compressors, columns and the like. A number of patents and publications are recited for disclosing aspects of a process of partially oxidizing isobutene or an isobutene equivalent into methacrylic acid in a single step or multi-step oxidation process, for example, U.S. Pat. No. 4,544,054; U.S. Pat. No.

4,618,709; U.S. Pat. No. 4,925,981; U.S. Pat. No. 4,956,493; U.S. Pat. No. 4,987,252; U.S. Pat. No. 5,356,460; U.S. Pat. No. 5,780,679 and WO 0345083.

U.S. Pat. No. 7,732,367 to Stevenson et al. concerns a catalyst for accomplishing the gas-phase methacrolein oxidation to methacrylic acid and methods of making the catalyst, where the catalyst includes at least molybdenum, phosphorus, vanadium, bismuth and a first component selected from potassium, rubidium, cesium, thallium or mixtures or combinations of these, has at least 57% medium pores and a nitric acid to molybdenum ratio of at least 0.5 to 1 or a nitric acid to $Mo_{12}$ ratio of at least 6.0:1.

U.S. Pat. No. 5,231,226 to Hammon et al. also relates particularly to the gas-phase oxidation of methacrolein to methacrylic acid, disclosing a process for the catalytic gas-phase oxidation of methacrolein to methacrylic acid in a fixed-bed reactor at elevated temperature on catalytically-active oxides with a single pass conversion of from 45 to 95 percent. Because of the exothermicity of the reaction, the reaction temperature is maintained from 280 to 340 degrees Celsius until a methacrolein conversion of from 20 to 40 percent is reached, at which point the reaction temperature is reduced at once, incrementally or continuously by from 5 to 40 degrees Celsius until a conversion of from 45 to 95 percent has been accomplished, with the proviso that the reaction temperature is not less than 260 degrees Celsius. Suitable catalysts are indicated as those described in EP 265733, EP 102688 and DE 3010434.

U.S. Pat. No. 5,155,262 to Etzkorn et al. concerns both processes for the oxidation of isobutene to methacrolein and for the oxidation of isobutene to methacrylic acid in two stages with methacrolein as an intermediate, wherein prior methods using steam in the starting reactant gas mixture to avoid flammable gas mixtures and to improve reaction selectivity are assertedly improved by using essentially inert, essentially anhydrous diluent gases in place of the steam. Reduced wastewater load, improved selectivity and reduced byproduct formation are said to result from the substitution. Etzkorn et al. recite that "many oxidation catalysts have been disclosed for producing methacrolein in high yield by oxidizing isobutene", col. 1, lines 60-62, giving as examples catalysts containing mixed oxides of molybdenum, bismuth and iron with phosphorus or tungsten or antimony, and commonly incorporating cobalt and/or nickel and alkali metals as promoters, col. 1, lines 62-65. For the second stage oxidation of methacrolein to methacrylic acid, mixed metal oxide catalysts are described which are said to typically contain molybdenum, vanadium, tungsten, chromium, copper, niobium, tantalum and antimony. Etzkorn et al. refer in this regard to a number of additional publications predating those listed in U.S. Pat. No. 8,273,313, including U.S. Pat. No. 4,147,885; U.S. Pat. No. 3,475,488; U.S. Pat. No. 3,171,859; U.S. Pat. No. 4,267,386 and U.S. Pat. No. 4,267,385, as well as UK 2,068,947 and U.S. Pat. No. 4,618,709.

Figure 2:
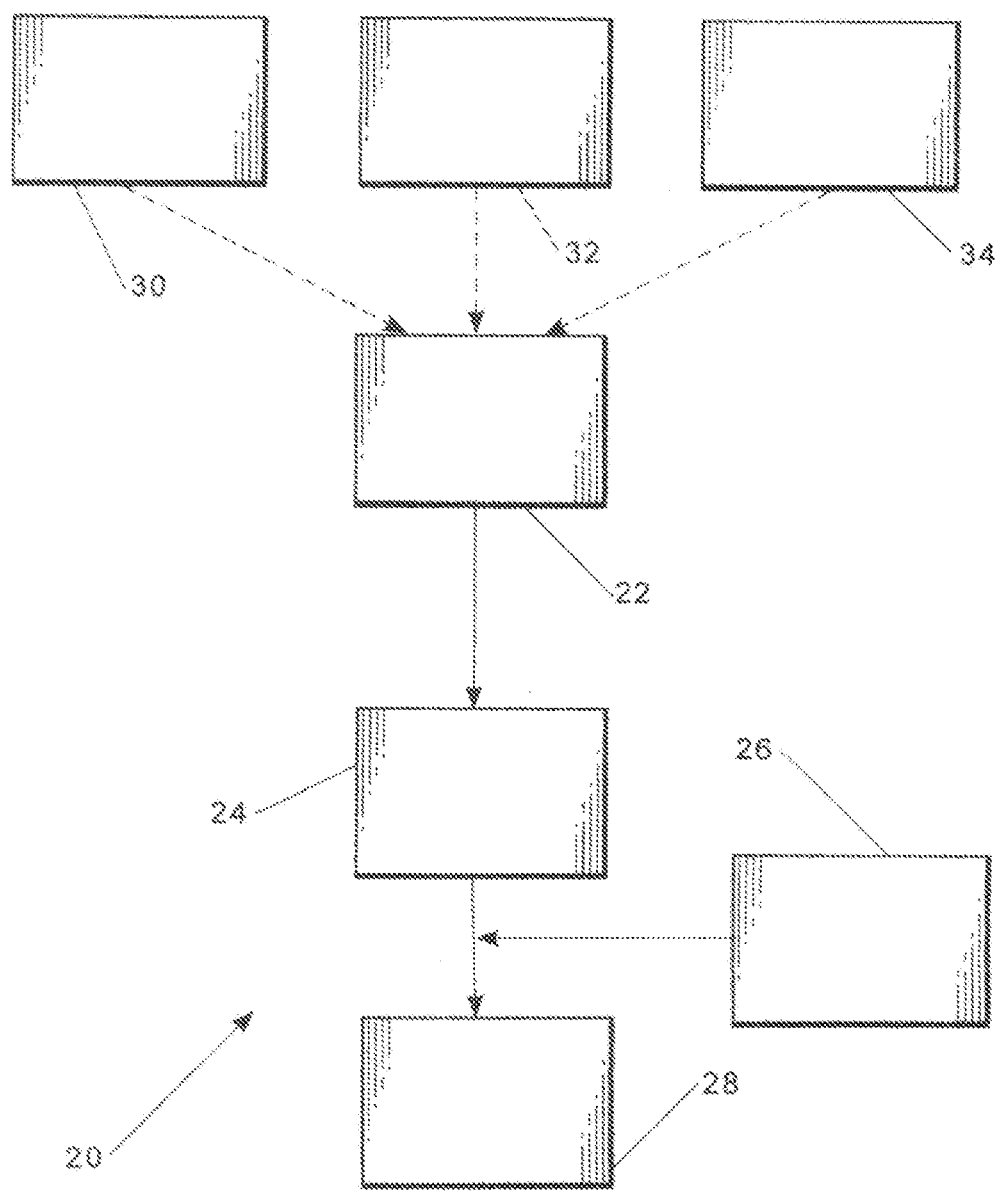
FIG. 2 schematically depicts a process for producing a biobased methacrylic acid, particularly a wholly biobased methacrylic acid, from a biobased and especially a wholly biobased isobutene made from acetic acid, according to the second aspect of the present invention as summarized above.

Turning now to FIG. 2, a process is schematically illustrated according to a second aspect of the present invention, providing biobased and preferably wholly biobased methacrylic acid via methacrolein from a corresponding biobased and preferably wholly biobased isobutene, wherein the isobutene is prepared from acetic acid in the presence of a catalyst, the biobased isobutene is oxidized to methacrolein and the methacrolein is oxidized to methacrylic acid. In certain embodiments, the catalyst is a $Zn_xZr_yO_z$ mixed oxide catalyst, especially a catalyst made by a process as described in the '433 application, and the process of making the starting biobased isobutene is carried out as described in the incorporated '312 application.

More particularly, a process 20 is shown wherein acetic acid 22 is converted to isobutene 24, and the isobutene 24 is oxidized (as described above in connection with FIG. 1) using oxygen from an oxygen source 26 to provide a methacrylic acid product 28. As further described in the '312 application and as is well appreciated by those skilled in the art, the acetic acid 22 can be obtained by various methods from a number of starting materials. If desired, at least a portion of the acetic acid that is conventionally produced in the oxidation of isobutene 24 through methacrolein to the methacrylic acid product 28 can be recovered and recycled to form a portion of the acetic acid 22 that is used.

For example, the acetic acid 22 can be produced from a source 30 of five and six carbon sugars by fermentation. U.S. Pat. No. 6,509,180 and U.S. Pat. No. 8,252,567 seek to improve upon known processes for making ethanol and butanol/hexanol, respectively, by means including the fermentation of five and six carbon sugars into acetic acid. In U.S. Pat. No. 6,509,180, the acetic acid is esterified to form an acetate ester which may then be hydrogenated (using hydrogen from, e.g., steam reforming of natural gas, electrolysis of water, gasification of biomass or partial oxidation of hydrocarbons generally) to ethanol. In U.S. Pat. No. 8,252,567, the ethanol formed in this manner can be used to make butanol and hexanol, by subjecting the ethanol with acetate, acetic acid or mixtures thereof to an acidogenic fermentation using, for example, species of the bacteria *Clostridium* (*Clostridium kluyveri* is mentioned), to produce butyrate, butyric acid, caproate, caproic acid or mixtures thereof. These materials then in turn are acidified to convert butyrate and caproate to butyric acid and caproic acid, the butyric and caproic acids are esterified and then the butyric and caproic acid esters undergo reduction by hydrogenation, hydrogenolysis or reduction by carbon monoxide to provide butanol and ethanol.

As related in these two patents and as is well known to those skilled in the fermentation art, the fermentation of the five and six carbon sugars 30 to form acetic acid 22 can be accomplished by various organisms. More particularly, homoacetogenic microorganisms are able through fermentation to produce acetic acid with 100% carbon yield; these microorganisms internally convert carbon dioxide to acetate, in contrast to a process for producing ethanol from sugars obtained from biomass, wherein carbon dioxide is produced as a byproduct.

Examples of homoacetogens given by U.S. Pat. No. 8,252,567 are microorganisms of the genus *Moorella* and *Clostridium*, especially microorganisms of the species *Moorella thermoaceticum* (described as formerly classified as *Clostridium thermoaceticum*) or *Clostridium formicoaceticum*. U.S. Pat. No. 8,252,567 represents that about one hundred known acetogens in twenty-two genera were known as of 2009, and cross-references Drake, et al., Ann. N.Y. Acad. Sci. 1125: 100-128 (2008) for a review of acetogenic microorganisms.

Other references describing fermentation methods for producing acetic acid from five and six carbon sugars include U.S. Pat. No. 4,935,360; U.S. Pat. No. 8,236,534; U.S. Pat. No. 4,513,084; U.S. Pat. No. 4,371,619 and U.S. Pat. No. 4,506,012; both one-step fermentation processes from the sugars to acetic acid, acetates or both are disclosed, as well as two-step processes involving a first fermentation to lactic acid (by *lactobacillus* or known methods of homolactic fermentation, preferably) followed by a second fermentation to convert lactic acid to acetic acid, for example, using *Clostridium formicoaceticum*.

Any of the known fermentation methods may, in short, be used as described in the '312 application to produce acetic acid 22 for conversion to isobutene 24 in the presence of the $Zn_xZr_yO_z$ mixed oxide catalysts, but homoacetogenic fermentation methods are considered preferable in that carbon dioxide is not produced as a byproduct—the carbon dioxide represents a yield loss from the overall process to make isobutene and as a greenhouse gas is undesirable particularly in the context of a process to make a needed product more sustainably from renewable resources.

As well or in the alternative, the acetic acid feedstock 22 can be made from ethanol 32, according to any of several known methods employing oxidative fermentation with acetic acid bacteria of the genus *Acetobacter*.

As well or in the alternative, the acetic acid feedstock 22 can be made from methanol 34 through combination with carbon monoxide according to the most industrially used route for making acetic acid, for example, in the presence of a catalyst under conditions effective for the carbonylation of methanol. A variety of carbonylation catalysts are known in this regard, see, for example, U.S. Pat. No. 5,672,743; U.S. Pat. No. 5,728,871; U.S. Pat. No. 5,773,642; U.S. Pat. No. 5,883,289; U.S. Pat. No. 5,883,295.

In regard to the production of methanol 34, with increasing concerns for the abatement of greenhouse gases such as carbon dioxide in recent years, a substantial amount of work has been reported on methods to convert carbon dioxide to methanol, see, for example, Wesselbaum et al., "Hydrogenation of Carbon Dioxide to Methanol by Using a Homogeneous Ruthenium-Phosphine Catalyst", *Angew. Chem. Int. Ed.*, vol. 51, pp 7499-7502 (2012); Ma et al., "A Short Review of Catalysis for $CO_2$ Conversion", *Catalysis Today*, vol. 148, pp 221-231 (2009); Borodko et al., "Catalytic Hydrogenation of Carbon Oxides—a 10-Year Perspective", *Applied Catalysis A: General*, vol. 186, pp 355-362 (1999); and U.S. Pat. No. 8,212,088 to Olah et al., "Efficient and Selective Chemical Recycling of Carbon Dioxide to Methanol, Dimethyl Ether and Derived Products" and the various additional references cited in each of these. Those skilled in the art will thus be well-acquainted with processes and associated catalysts for producing methanol 34 from carbon dioxide (such as may be produced in the production of ethanol 32 by fermentation or recovered from combustion processes or other industrial emissions) and from carbon dioxide, carbon monoxide and hydrogen derived from the gasification of a biomass, though it will be appreciated that methanol 34 or these "building block" gases can alternately or additionally be obtained from a biomass by anaerobic digestion through methane, from electrolysis of water using energy from geothermal sources, by electrolytic cleavage of carbon dioxide to produce carbon monoxide and water and so forth. As well, it will be appreciated that the methanol 34 could be prepared from methane from natural gas, but preferably a substantial proportion and more preferably all of the methanol 34 used will be wholly biobased.

The production of the more stable mixed oxide catalysts of the '433 application and the use of mixed oxide catalysts to convert both of ethanol and acetic acid to isobutene are demonstrated for purposes of illustration in the following non-limiting examples:

Example 1

Commercial zirconium hydroxide was dried at 120 degrees Celsius for more than 5 hours. Calculated amounts of $Zn(NO_3)_2$ (from Sigma-Aldrich, more than 99.8 percent purity) were dissolved in water to form a series of clear solutions. Dried zirconium hydroxide (also from Sigma-Aldrich, more than 99.8 percent purity) was then mixed with the solutions in turn by incipient wetness, in order to form wet powders impregnated with Zn in certain proportions to the zirconium in the form of the dried zirconium hydroxide powder. The wetted powders were then dried at 80 degrees Celsius for 4 hours, followed by calcination at 400 degrees Celsius for 2 hours and at 600 degrees Celsius for 3 hours to obtain a series of $Zn_xZr_yO_z$ catalysts.

Ethanol to isobutene runs were conducted with the catalysts thus prepared in a fixed-bed stainless steel reactor, having an inside diameter of 5 millimeters. A given amount of catalyst was packed between quartz wool beds. A thermocouple was placed in the middle of the catalyst bed to monitor the reaction temperatures. Before beginning the reaction, the catalyst beds were first pretreated by flowing 50 ml/minute of nitrogen at 450 degrees Celsius through the catalyst over a half hour, then a mixture of ethanol/water at steam to carbon ratios from 1 to 5 was introduced into an evaporator at 180 degrees Celsius by means of a syringe pump and carried into the reactor by the flowing nitrogen carrier gas. Meanwhile, the product line was heated to in excess of 150 degrees Celsius before a cold trap, to avoid condensing the liquid products in the product line.

A Shimadzu 2400 gas chromatograph equipped with an auto sampling valve, HP-Plot Q column (30 m, 0.53 mm, 40 µm) and flame ionization detector was connected to the line between the reactor outlet and cold trap to collect and analyze the products in the effluent gas. After the cold trap, an online micro-GC (MicroGC 3000A equipped with molecular sieves 5A, plot U columns and thermal conductivity detectors) was used to analyze the product gases specifically, using nitrogen as a reference gas.

An ethanol/water solution (steam to carbon ratio of 2.5) was then supplied by flowing $N_2$ to the reactor at a weight hourly space velocity (WHSV) of 0.95 $hr^{-1}$. The ethanol concentration was 15.1 percent by weight, and the reaction temperature was 450 degrees Celsius. Ethanol conversion was 100% throughout, and isobutene selectivity declined by less than 2 percent over 200 hours on stream for the series of catalysts prepared as described.

Thermogravimetric and differential scanning calorimetry analysis of the recovered, spent catalysts showed only about 0.7 weight percent of coke after 207 hours onstream.

Example 2

Commercial zirconium hydroxide was dried at 120 degrees Celsius for more than 5 hours. A calculated amount of $Zn(NO_3)_2$ (from Sigma-Aldrich, more than 99.8 percent purity) was dissolved in water, forming a clear solution. The dried zirconium hydroxide (which was also from Sigma-Aldrich, more than 99.8 percent purity) was then mixed with the solution by incipient wetness, in order to form wet powders impregnated with Zn. The wetted powder was then dried at 80 degrees Celsius for 4 hours, followed by calcination at 550 degrees Celsius for 3 hours, to obtain a $Zn_1Zr_8O_z$ catalyst.

An acetic acid to isobutene process was conducted with the catalyst thus prepared in a fixed-bed stainless steel reactor having an inside diameter of 5 millimeters. 100 mg of the catalyst was packed between quartz wool beds. A thermocouple was placed in the middle of the catalyst bed to monitor the reaction temperature. Before beginning the reaction, the catalyst bed was pretreated by flowing 50 ml/minute of nitrogen at 450 degrees Celsius through the catalyst over a half hour. A 25 weight percent solution of acetic acid in water was then introduced into an evaporator at 180 degrees Celsius by means of a syringe pump, and the vaporized steam/acetic acid was carried into the reactor by a flowing nitrogen carrier gas at an acetic acid concentration in the gas phase of 1.36 weight percent and a WHSV of 0.1 grams of acetic acid per gram of catalyst per hour. Meanwhile, the product line was heated to in excess of 150 degrees Celsius before a cold trap, to avoid condensing the liquid products in the product line. A reaction temperature of 415 degrees Celsius was employed.

A Shimadzu 2400 gas chromatograph equipped with an auto sampling valve, HP-Plot Q column (30 m, 0.53 mm, 40 μm) and flame ionization detector was connected to the line between the reactor outlet and cold trap to collect and analyze the products in the effluent gas. After the cold trap, an online micro-GC (MicroGC 3000A equipped with molecular sieves 5A, plot U columns and thermal conductivity detectors) was used to analyze the product gases specifically, using nitrogen as a reference gas.

A consistent product of about 5 percent by weight of methane, about 10 percent by weight of acetone, about 33 percent by weight of carbon dioxide and more than about 50 percent by weight of the desired isobutene product was obtained; in contrast to the ethanol to isobutene process using these same $Zn_xZr_yO_z$ mixed oxide catalysts in Example 1, no ethylene or propylene was produced. The catalyst showed very high stability over the full duration of the run, with no signs of observable deactivation after more than 1400 minutes of time-on-stream operation.

Examples 3 Through 31

A number of additional catalysts were prepared by first drying commercial zirconium hydroxide at 120 degrees Celsius for more than 5 hours. Calculated amounts of $Zn(NO_3)_2$ (from Sigma-Aldrich, more than 99.8 percent purity) were dissolved in water to form a series of clear solutions. The dried zirconium hydroxide (also from Sigma-Aldrich, more than 99.8 percent purity) was then mixed with the solutions in turn by incipient wetness, in order to form wet powders impregnated with Zn in certain proportions to the zirconium in the form of the dried zirconium hydroxide powder. The wetted powders were then dried at 80 degrees Celsius for 4 hours, followed by calcination at the temperature indicated in Table 1 below for 3 hours, to obtain a series of $Zn_xZr_yO_z$ catalysts by an incipient wetness method. These catalysts were used to convert ethanol to isobutene in the manner of Example 1. Particular reaction conditions, whether the reaction temperature, WHSV or steam to carbon ratio, for example, were varied to compare the effect on the selectivities to acetone and isobutene at full conversion of the ethanol. For several of the catalysts, some amount of sulfur was purposely doped into the catalyst to assess the effect of sulfur at those certain levels on the selectivities to acetone and to isobutene. Thus, the catalyst for example 28 was doped with 10 ppm of sulfur, while for example 29 the catalyst was doped with 50 ppm of sulfur and for example 30 with 200 ppm (by weight).

TABLE 1

Additional Ethanol to Isobutene Runs

| Ex # | Zn/Zr ratios | Calcination temp (° C.) | Reaction temp (° C.) | WHSV ($g_{ethanol}/g_{catal}/hr$) | Steam to carbon ratio | Ethanol (gas wt %) | Acetone selectivity (mol %) | Isobutene selectivity (mol %) |
|---|---|---|---|---|---|---|---|---|
| 3 | 1/6.5 | 550 | 450 | 0.19 | 5 | 1.0 | 3.5 | 46.4 |
| 4 | 1/6.5 | 550 | 425 | 0.08 | 5 | 1.0 | 4.0 | 49.8 |
| 5 | 1/8 | 550 | 450 | 0.19 | 5 | 1.0 | 3.4 | 47.3 |
| 6 | 1/8 | 550 | 415 | 0.08 | 5 | 1.0 | 8.5 | 51.4 |
| 7 | 1/10 | 550 | 450 | 0.19 | 5 | 1.0 | 2.9 | 49.2 |
| 8 | 1/10 | 550 | 425 | 0.08 | 5 | 1.0 | 3.8 | 51.5 |
| 9 | 1/12 | 550 | 450 | 0.19 | 5 | 1.0 | 2.5 | 48.9 |
| 10 | 1/12 | 550 | 450 | 0.08 | 5 | 1.0 | 0.5 | 45.5 |
| 11 | 1/12 | 550 | 425 | 0.08 | 5 | 1.0 | 3.8 | 51.6 |
| 12 | 1/12 | 550 | 415 | 0.08 | 5 | 1.0 | 6.2 | 51.3 |
| 13 | 1/14 | 550 | 450 | 0.19 | 5 | 1.0 | 4.9 | 46.8 |
| 14 | 1/10 | 500 | 450 | 0.19 | 5 | 1.0 | 0.7 | 47.6 |
| 15 | 1/10 | 500 | 475 | 0.19 | 5 | 1.0 | 0 | 41.9 |
| 16 | 1/10 | 500 | 450 | 0.08 | 5 | 1.0 | 0 | 42.7 |
| 17 | 1/10 | 500 | 425 | 0.08 | 5 | 1.0 | 1.2 | 49.3 |
| 18 | 1/10 | 600 | 475 | 0.19 | 5 | 1.0 | 7.2 | 42.3 |
| 19 | 1/10 | 600 | 450 | 0.19 | 5 | 1.0 | 13.7 | 42.1 |
| 20 | 1/10 | 600 | 450 | 0.08 | 5 | 1.0 | 4.3 | 43.8 |
| 21 | 1/10 | 600 | 425 | 0.08 | 5 | 1.0 | 12.9 | 44.8 |
| 22 | 1/10 | 600 | 400 | 0.08 | 5 | 1.0 | 32.6 | 33.1 |
| 23 | 1/10 | 650 | 450 | 0.19 | 5 | 1.0 | 32.2 | 30.1 |
| 24 | 1/10 | 650 | 450 | 0.08 | 5 | 1.0 | 10.6 | 41.8 |
| 25 | 1/10 | 650 | 425 | 0.19 | 5 | 1.0 | 44.9 | 23.0 |
| 26 | 1/10 | 650 | 425 | 0.08 | 5 | 1.0 | 26.1 | 37.4 |
| 27 | 1/10 | 650 | 415 | 0.08 | 5 | 1.0 | 34.1 | 32.3 |
| 28 | 1/10 | 550 | 415 | 0.08 | 5 | 1.0 | 7.3 | 52.1 |
| 29 | 1/10 | 550 | 415 | 0.08 | 5 | 1.0 | 6.3 | 52.4 |
| 30 | 1/10 | 550 | 415 | 0.08 | 5 | 1.0 | 8.4 | 51.2 |
| 31 | 1/8 | 550 | 450 | 0.31 | 2.5 | 15.0 | 2.8 | 53.5 |

Examples 32 Through 40

For these additional examples of converting acetic acid to isobutene, additional $Zn_xZr_yO_z$ mixed oxide catalysts were prepared both by the incipient wetness method (IW in Table 2 below) but also by the prior art hard template method (HT), and these were evaluated and the products analyzed using the same apparatus and method described above but under different sets of reaction conditions (as summarized in Table 2 below).

TABLE 2

Further Acetic acid to Isobutene Examples

| Ex # | Catalyst | Zn/Zr ratio | Reaction temp. (° C.) | WHSV ($g_{acetic}$/$g_{catal}$/hr) | Steam to carbon ratio | $C_{G\text{-}acetic\ acid}$ (wt %) | Acetone selectivity (mol %) | Isobutene selectivity (mol %) |
|---|---|---|---|---|---|---|---|---|
| 32 | HT | 1/15 | 450 | 0.25 | 5 | 1.3 | 30.5 | 41.7 |
| 33 | HT | 1/15 | 450 | 1.14 | 5 | 1.5 | 61.1 | 18.4 |
| 34 | IW | 1/8 | 415 | 0.1 | 5 | 1.4 | 9.8 | 52.5 |
| 35 | IW | 1/10 | 415 | 0.95 | 5 | 22.3 | 50.8 | 20.1 |
| 36 | IW | 1/10 | 450 | 0.16 | 2.5 | 18.8 | 0.7 | 50.6 |
| 37 | IW | 1/10 | 450 | 0.65 | 2.5 | 18.8 | 8.3 | 46.9 |
| 38 | IW | 1/10 | 415 | 0.16 | 2.5 | 18.8 | 5.7 | 57.2 |
| 39 | IW | 1/10 | 415 | 0.33 | 2.5 | 18.8 | 16.4 | 45.3 |
| 40 | IW | 1/10 | 415 | 0.65 | 2.5 | 18.8 | 30.5 | 35.0 |

The invention claimed is:

1. A process for making methacrylic acid via methacrolein from a biobased isobutene, comprising: in a single, first step and without isolating any intermediate species, converting acetic acid to isobutene in the presence of a mixed oxide catalyst comprised of oxides of Zn and Zr in which the ratio of Zn:Zr is from about 1:100 to about 10:1; oxidizing the isobutene to methacrolein with a source of oxygen in the presence of a catalyst; and further oxidizing methacrolein to methacrylic acid with a source of oxygen in the presence of a catalyst.

2. The process of claim 1, wherein the mixed oxide catalyst used in converting acetic acid to isobutene contains less than 0.14 percent by weight of sulfur.

3. The process of claim 2, wherein the catalyst contains less than 0.01 percent by weight of sulfur.

4. The process of claim 3, wherein the catalyst contains less than 0.001 percent by weight of sulfur.

* * * * *